United States Patent [19]

Fenn

[11] Patent Number: 5,810,888
[45] Date of Patent: Sep. 22, 1998

[54] THERMODYNAMIC ADAPTIVE PHASED ARRAY SYSTEM FOR ACTIVATING THERMOSENSITIVE LIPOSOMES IN TARGETED DRUG DELIVERY

[75] Inventor: Alan J. Fenn, Wayland, Mass.

[73] Assignee: Massachusetts Institute of Technology, Cambridge, Mass.

[21] Appl. No.: 882,985

[22] Filed: Jun. 26, 1997

[51] Int. Cl.[6] .................................................. A61M 5/00
[52] U.S. Cl. ........................................ 607/154; 600/407
[58] Field of Search .......................... 601/2, 3; 600/407, 600/439; 607/96, 154; 424/489, 423

[56] References Cited

U.S. PATENT DOCUMENTS

| 5,094,854 | 3/1992 | Ogawa et al. | 424/423 |
|---|---|---|---|
| 5,190,766 | 3/1993 | Ishihara | 424/489 |
| 5,251,654 | 10/1993 | Fenn . | |
| 5,441,532 | 8/1995 | Fenn . | |
| 5,540,737 | 7/1996 | Fenn . | |

OTHER PUBLICATIONS

Kawai et al., Cancer, "Direct Measurement of Doxorubicin Concentration in the Intact, Living Single Cancer Cell during Hyperthermia", vol. 79, No. 2, pp. 214–219, Jan. 15, 1997.

Time, "Gene Therapy: How it Works", p. 26, Fall 1996.

Bassett, et al., The Journal of Urology, "Treatment of Experimental Bladder Cancer with Hyperthermia and Phase Transition Liposomes Containing Methotrexate" vol. 139, pp. 634–636, Mar. 1988.

Hung et al., Cancer Research, "Liposomes and Hyperthermia in Mice: Increased Tumor Uptake and Therapeutic Efficacy of Doxorubicin in Sterically Stabilized Liposomes", vol. 54, pp. 2186–2191, Apr. 15, 1994.

Huang et al., Radiation Research Society—41st Annual Meeting, North American Hyperthermia Society 13th Annual Meeting, "Heat Activation of Liposome Drug Delivery", 1993.

Science, "Design of Liposomes for Enhanced Local Release of Drugs by Hyperthermia", vol. 202, No. 22, pp. 1290–1293, Dec. 1978.

Science, "Liposomes and Local Hyperthermia: Selective Delivery of Methotrexate to Heated Tumors", vol. 204, No. 13, Apr. 1979.

*Primary Examiner*—Marvin M. Lateef
*Assistant Examiner*—Eleni Mantis Mercader
*Attorney, Agent, or Firm*—Samuels, Gauthier, Stevens & Reppert

[57] ABSTRACT

A thermodynamic therapy system including a thermally activated drug delivery system which is provided within the bloodstream of a patient under therapy, and an adaptive phased array radiation transmission system operable for transmitting and focusing radiation to heat a treatment area within the patient. The drug delivery system releases a selected drug at the treatment area in response to the treatment area being heated by the focused radiation.

28 Claims, 5 Drawing Sheets

THERMODYNAMIC ADAPTIVE PHASED ARRAY SYSTEM FOR ACTIVATING THERMOSENSITIVE LIPOSOMES IN TARGETED DRUG DELIVERY

This invention was made with government support under Grant No. F19628-95-C-0002 awarded by the U.S. Air Force. The government has certain rights in the invention.

BACKGROUND OF THE INVENTION

The present invention generally relates to a minimally invasive RF, microwave, or ultrasound thermodynamic adaptive phased array system used in combination with thermosensitive liposomes and pharmaceutical agents, for minimally invasive targeted treatment of large tumor masses, as well as the treatment of large-volume infected or arthritic tissue or other diseased tissue deep within the human body. The thermodynamic adaptive phased array produces heat which activates thermosensitive liposomes and releases drugs in targeted tissue in accordance with the invention. It is appropriate and descriptive to refer to the invention as an adaptive thermodynamic therapy or ATDT.

The successful treatment of breast tumors, head and neck tumors, prostate tumors and other deep seated tumors (malignant or benign) within the human body is a difficult task. The main objective of the treatment is to reduce in size or completely remove the tumor mass by one or more modalities available at the treatment facility. The most common modalities are surgery, radiation therapy and chemotherapy. Surgical treatment of breast cancer often involves substantial disfigurement, and surgery for other deep seated cancers often creates complications for surrounding vital organs and healthy tissue. Radiation therapy of deep seated tumors also puts surrounding healthy tissues at risk.

A modality used alone or in combination with one of the above modalities is "tissue heating" or hyperthermia. In particular, it is well known from clinical trials in humans that hyperthermia combined with X-ray therapy improves malignant tumor complete response by a factor of two compared to X-ray therapy alone. Hyperthermia is known to have a greater effect on benign tumors or tumor cells in S-phase compared to radiation therapy. The S-phase represents about 40-percent of the cell cycle, so radiation therapy fails to kill many tumor cells during any given radiation therapy treatment session. Hyperthermia applied either simultaneously with radiation therapy or within a period of about one hour prior to radiation therapy is particularly effective in improving tumor complete responses.

Clinical trials in humans have also shown that substantial improvements in tumor response can be achieved when hyperthermia is combined with chemotherapy. Chemotherapy, delivered systemically through the blood stream, is known to have toxic side effects on both cancerous and healthy tissues exposed to the chemotherapy agent. Methods of targeting the chemotherapy agent to the tumor while sparing adjacent healthy tissue are desirable.

Thermosensitive liposomes, have been known to have the capability of encapsulating chemotherapy agents and releasing these agents into heated tissue. Recently, successful targeted chemotherapy delivery to brain tumors in animals using thermosensitive liposomes has been demonstrated as described in K. Kakinuma et al, "Drug delivery to the brain using thermosensitive liposome and local hyperthermia", International J. of Hyperthermia, Vol. 12, No. 1, pp. 157–165, 1996. Kakinuma's study was conducted by using an invasive needle hyperthermia RF antenna placed directly within the tumor to locally heat the tumor and the liposomes. The results showed that when thermosensitive liposomes are used as the drug carrier, significant chemotherapy drug levels were measured within brain tumors that were heated to the range of about 41° to 44° C. Presumably, thermosensitive liposomes can be developed to deliver chemotherapy drugs and genetic drugs to other body sites such as the breast, neck, prostate, and others. A specific formulation for a thermosensitive liposome is described in U.S. Pat. No. 5,094,854, however, there is no consideration of the method of delivery of deep heat.

It is documented in the literature that it is difficult to deliver drugs to solid tumors in the human body. For example, abnormal vessels in tumors can restrict local blood flow in tumors and, hence, impede the delivery of drugs to the tumor. Abnormally elevated pressure within the tumor is also known to retard the passage of drug molecules from the blood stream into the tumor. The invention is intended to increase the concentration of a drug within the tumor by means of targeted heating of thermosensitive liposomes containing the drug.

With hyperthermia, a controlled thermal dose distribution is required for effective treatment of a deep-seated tumor. Typical localized-hyperthermia temperatures required for therapeutic treatment of cancer are in the 42.5°–45° C. range which must be maintained for approximately 30 to 60 minutes. Healthy tissue, generally, should be kept at temperatures below 42.5° C. during the treatment. For targeted chemotherapy drug delivery, temperatures in the range of about 40° to 45° C. have been demonstrated to be effective on tumors.

SUMMARY OF THE INVENTION

An adaptive thermodynamic phased array antenna surrounds a target body and provides minimally invasive heating of tissue, in the range of 40 to 45 degrees Celsius, to activate thermosensitive liposomes and preferentially deliver drugs to regions heated deep within the body. The thermosensitive liposomes, which encapsulate the pharmaceutical agents, are injected into the blood stream where they remain stable until they reach an area heated by the thermodynamic phased array. Upon reaching the heated area, the thermosensitive liposomes release their encapsulated drug which treats a cancerous tumor or infected/diseased area of the body. The power and phase delivered to the phased array antenna elements are computer controlled using feedback signals measured by noninvasive electric-field sensors, placed on the patient's skin surface and within the tissue region to be treated, and by using an adaptive nulling and focusing gradient search algorithm. Additionally, the total RF power delivered to the phased array is modified using temperature feedback to generate the desired temperature distribution within the tumor or infected tissue to heat the thermosensitive liposomes.

The use of adaptive phased arrays permits heating of large tissue masses deep within the torso of the human body and, at the same time, avoid heating of surrounding healthy tissues in the body. Thus, thermosensitive liposomes can be activated and pharmaceutical agents released throughout the large tissue mass by means of the noninvasive adaptive phased array. Adaptive nulls formed away from the tumor in healthy tissue regions prevent the thermosensitive liposomes from being activated and, hence, pharmaceutical agents are not substantially released into the healthy tissues. Applications for this disclosure include cancer treatment and the treatment of infection and arthritis.

In accordance with an exemplary embodiment of the invention there is provided a thermodynamic therapy system including a thermally activated drug delivery system which is provided within the bloodstream of a patient under therapy, and an adaptive phased array radiation transmission system operable for transmitting and focusing radiation to heat a treatment area within the patient. The drug delivery system releases a selected drug at the treatment area in response to the treatment area being heated by the focused radiation.

DETAILED DESCRIPTION OF THE ILLUSTRATED EMBODIMENTS

Figure 1:
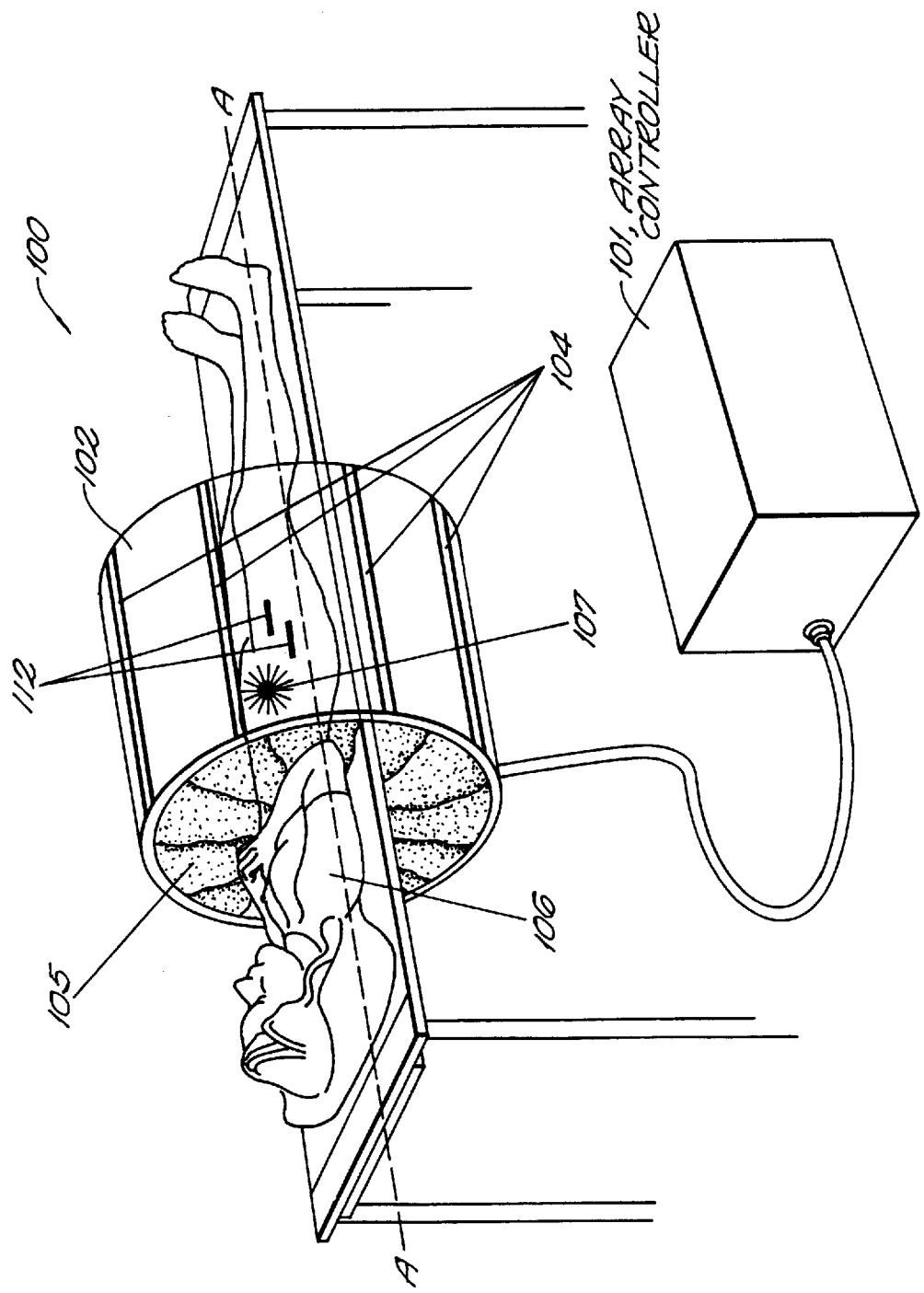
FIG. 1 is a perspective view of a minimally invasive adaptive RF phased array thermodynamic system for treating deep seated tumors within a patient or target body to target the delivery of thermosensitive liposomes containing pharmaceutical agents in accordance with an exemplary embodiment of the invention.

The most difficult aspect of implementing thermodynamic therapy, with either microwave or radio-frequency (RF) energy, is producing sufficient heating at depth. Noninvasive multiple-applicator RF adaptive phased arrays with invasive and noninvasive electric-field probes can be used for producing an adaptively focused beam at the tumor position with adaptive nulls formed in healthy tissues as described in U.S. Pat. Nos. 5,251,645, 5,441,532, and 5,540,737, all of which are incorporated herein by reference. Ideally, a focused RF radiation beam is concentrated at the tumor with minimal energy delivered to surrounding healthy tissue.

As the thermodynamic antenna beam diameter is proportional to the electric-field wavelength, a small focal region suggests that the radiating wavelength be as small as possible. However, due to propagation losses in tissue, the electromagnetic wave depth-of-penetration decreases with increasing transmit frequency. For example, a radiating frequency of 915 MHz is used for noninvasive treatment of tumors up to about 3 cm beneath the skin surface. Lower radio frequencies such as 100 MHz are used for noninvasive treatment of deep seated tumors up to about 15 cm beneath the skin surface.

One of the significant problems in heating a tumor with a noninvasive conventional hyperthermia antenna is the formation of undesired "hot spots" in surrounding tissue. This additional undesired heating often produces pain, burns, and blistering in the patient, which requires terminating the treatment. Similar difficulties of unintentionally irradiating superficial tissue with noninvasive X-ray applicators are encountered during deep tumor treatments. Thus, techniques for safely administering thermodynamic therapy to the deep tumor site with noninvasive applicators are needed.

U.S. Pat No. 5,251,645, incorporated herein by reference, describes an adaptive RF hyperthermia phased array which uses feedback measurements from noninvasive electric field sensors to null or reduce undesirable hot spots in healthy tissue, while focusing the array radiation using measurements from an invasive electric field sensor in the tumor. A gradient search algorithm is used in controlling the power and phase delivered to the adaptive RF array radiating elements. Computer simulations showed the viability of the adaptive nulling phased array for treating deep seated tumors.

U.S. Pat. No. 5,441,532, incorporated herein by reference, describes a monopole phased array device used to heat deep seated tumors using adaptive RF or microwave focusing while simultaneously minimizing the occurrence of healthy tissue hot spots using adaptive nulling. Experimental data for an RF adaptive hyperthermia phased array system with both homogeneous and heterogeneous phantoms showed the ability to minimize surface hot spots while irradiating a deep seated tumor. Computer simulation data for a 915 MHz focused hyperthermia monopole phased array were presented.

U.S. Pat. No. 5,540,737, incorporated herein by reference, describes an adaptive monopole waveguide phased array on opposite sides of compressed breast tissue is used to heat deep seated breast tumors with microwave energy. Experimental deep focusing electric-field data for the monopole phased array breast hyperthermia system at 915 MHz were shown to be in good agreement with computer simulations.

A brief description of the relationship between the RF energy absorption and temperature rise in tissue is now described. Electromagnetic energy absorption in tissue, sometimes referred to in the literature as the SAR (specific absorption rate or absorbed power per unit mass), has units of Joules/kg-sec (or W/kg) and may be expressed as:

$$SAR = \frac{1}{2} \frac{\sigma}{\rho} |E|^2, \quad (1)$$

where $\sigma$ is the tissue electrical conductivity (S/m), $\rho$ is the tissue density (kg/m^3), and $|E|$ is the local electric-field magnitude (V/m). In equation (1), the quantity $\frac{1}{2}\sigma|E|^2$ is the time-average RF power density converted to heat energy, referred to as dissipated power.

If one ignores the body-specific thermal conduction and thermal convection effects, which are not important until after a significant temperature rise occurs, the initial temperature rise $\Delta T$(°C.) in tissue is related to the specific absorption rate by $$\Delta T = \frac{1}{c} SAR \Delta t, \quad (2)$$

where c is the specific heat of the tissue (joules/kg-deg C.), and $\Delta t$ is the time period of exposure (seconds). Substituting equation (1) in equation (2) yields a relation between the induced temperature rise in tissue and the applied electric field as $$\Delta T = \frac{1}{2} \frac{\sigma}{\rho c} |E|^2 \Delta t. \qquad (3)$$

Thus, by modifying the local electric-field amplitude, the local energy absorption and induced temperature rise in tissue are affected. For example, in malignant tissue it is desired to deposit an electric field of sufficient magnitude to heat the tumor volume to a temperature range that activates the local release of the pharmaceutical agent from the thermosensitive liposomes. During tumor treatments, it is desirable to limit the electric-field magnitude in healthy tissue to be less than that within the tumor, to keep the healthy tissue temperature below the temperature that activates the thermosensitive liposomes.

Liposomes are microscopic man-made lipid particles (organic compounds including the fats, fat-like compounds and the steroids) that can be engineered to entrap drugs, creating new pharmaceuticals with enhanced efficacy, better safety or both. Toxicity of effective drugs can be targeted to cancerous tumors through the use of liposome technology. Particular lipids are chosen to make liposomes with liquid-crystal phase transitions in the range of about 40° to 45° C. where the liposomes undergo abrupt changes in physical properties. In contrast, the same liposomes have little change in physical properties at temperatures between 40° C. and the 37° C. normal body temperature. Liposomes can have one or more aqueous compartments that contain the pharmaceutical agent. These aqueous compartments are enclosed by a lipid bilayer.

Nearly, total release of the liposome contents has been demonstrated in vitro, when the temperature of the liposome is raised to the range of the liquid-crystal phase transition for only a few seconds. For application to the human body, the liposomes are injected into the blood stream and as the liposomes circulate within the small arteries, arterioles, and capillaries repeatedly through an area heated for 30 to 60 minutes, the drug contents of the liposomes are released in significantly higher levels than in areas that do not receive heat. Drug uptake enhancement for heated tumors in animal studies is 3 to 4 times higher in the phase-transition heated areas compared to areas having temperatures lower than the phase-transition temperature. The liposome phase transition is due to an increase in motion about the C—C bonds of the fatty acyl chains, which pass from a highly-ordered, gel-like state to a more mobile fluid state. During the gel-to-fluid phase transition, thermal energy is absorbed which effectively melts the bilayer enclosing the aqueous spaces. A specific formulation for a thermosensitive liposome is described in U.S. Pat. No. 5,094,854, incorporated herein by reference.

There are a vast number of drugs used in treating cancer, infections, and arthritis. In the last several years, several genetic drugs (gene therapy) have been developed for treating cancer, infections, and arthritis. Gene therapy refers to the insertion of normal or genetically altered genes into diseased tissue areas, usually to replace defective genes. Patients with advanced lung cancer who have mutated copies of the tumor suppressor gene (p53) are injected with healthy genes into their lungs. Gene therapy (normal BRCA1 genes) is being developed for prostate cancer and breast cancer patients. Researchers are currently developing gene therapy for HIV (human immunodeficiency virus). Patients with rheumatoid arthritis suffer joint erosion and inflammation due to the biochemical degradation from interleukin-1 (IL-1). Gene therapy introduces cells containing a gene that blocks the attack from interleukin-1.

Heat shock induced specific gene activation is also well known. The function of heat shock proteins is to assist in binding other proteins and to assist in the translocation (or promotion) of these proteins across cellular membranes. Cells respond to heat stress by upregulating the transcription and translation of heat shock protein genes. Hyperthermia has been shown to provide an increased expression of heat shock protein promoters. The rapid and specific response of these thermoenhanced promoters provides targeted gene expression. The thermodymanic adaptive phased array system of the invention provides the means for targeted gene therapy.

The invention involves a unique combination of thermosensitive liposomes for targeted delivery of pharmaceutical agents with the use of minimally invasive adaptive nulling and focusing monopole phased arrays for adaptive thermodynamic therapy of a patient.

FIG. 1 is a perspective view of a minimally invasive adaptive RF phased array thermodynamic system 100 for treating deep seated tumors within a patient or target body 106 to target the delivery of thermosensitive liposomes containing pharmaceutical agents in accordance with an exemplary embodiment of the invention. An annular monopole or dipole phased array transmit antenna or phased array applicator 102 surrounds the patient's torso. The applicator 102, which is energized and controlled by an array controller 101, has a plurality of dipole transmit antenna elements 104 which are uniformly positioned around the patient. The monopole array applicator includes a metallic waveguide structure filled with deionized or distilled water. Each monopole or dipole antenna element is oriented parallel to the other monopole or dipole antenna elements and parallel to an axis A—A passing through the center of a cylinder or oval defined by applicator 102.

The patient is positioned within the thermodynamic phased array applicator 102 such that the deep-seated tumor 107 to be treated is at the approximate center, or focus, of the phased array applicator. A water bolus 105 is provided between the patient and the phased array applicator to control the temperature of the patient's skin and to efficiently couple RF energy into the patient. The phased array applicator 102 therapeutically illuminates the target body 106 with electric field (E-field) or electromagnetic energy radiated by the monopole or dipole antenna elements 104 focused on tumor 107 deep within the body.

In the adaptive thermodynamic phased array of the invention, electric-field nulls are used to reduce the power delivered to potential hot spots. Non-invasive field probes or sensors 112 are used on the surface of the target body 106 for the elimination of hot spots interior to the target tissue. With the adaptive thermodynamic phased array system of the invention and described herein, RF energy nulls are adaptively formed to reduce the electric field energy delivered to these potential hot spots. As will be described hereinafter, the energy nulls achieved by the adaptive nulling technique of the invention are both invasive to the target, i.e., extend into the target body, and non-invasive to the target, i.e., on the surface of the target.

Figure 2:
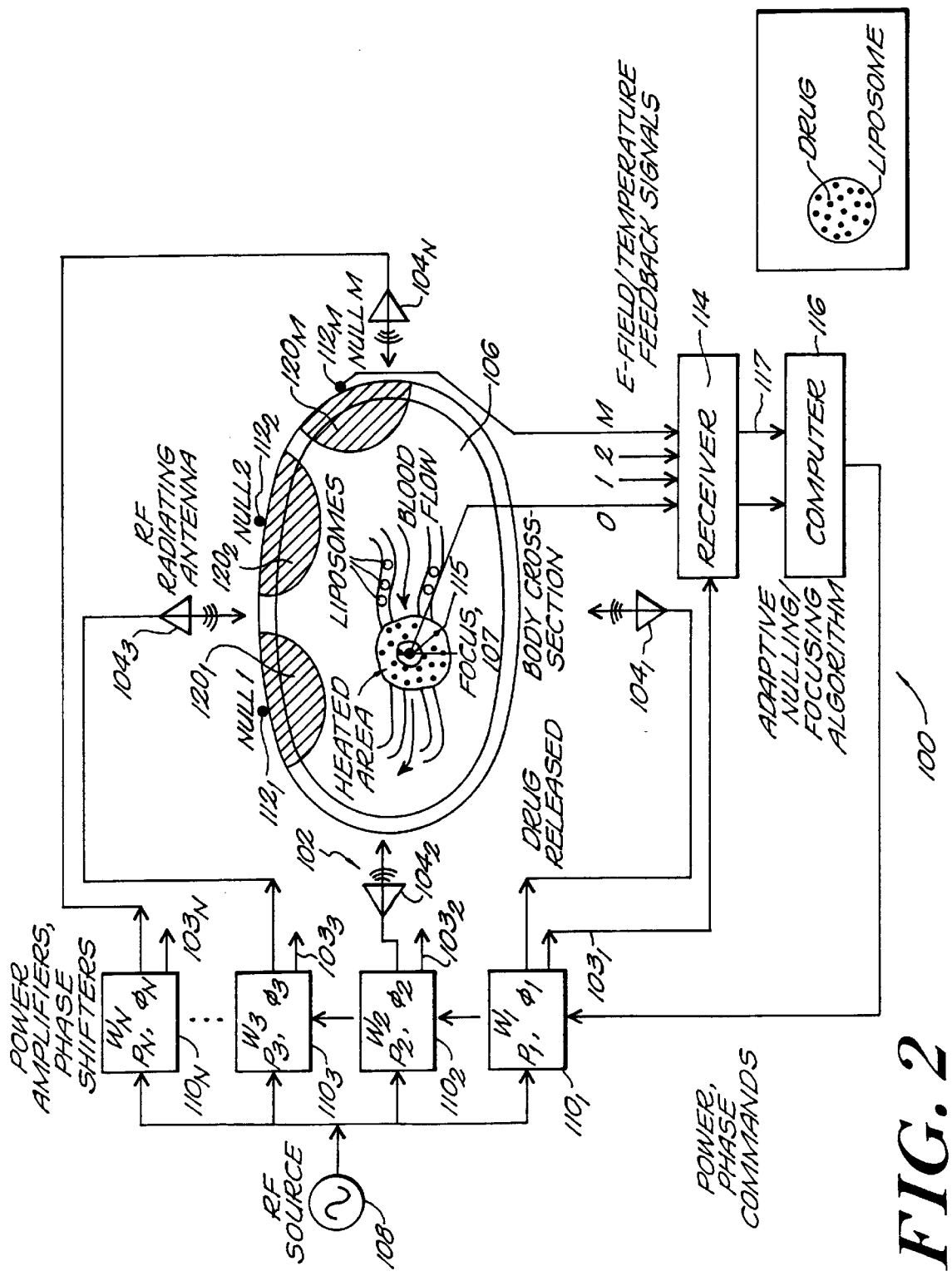
FIG. 2 is a schematic block diagram of the minimally invasive adaptive RF phased array thermodynamic system of FIG. 1.

Refer now to FIG. 2, a schematic block diagram of the minimally invasive adaptive RF phased array thermodynamic system 100 of FIG. 1 is shown. The system includes the phased array applicator 102 having a plurality of transmitting antenna elements $104_n$, where n=1, . . . , N, surrounding target body 106 for focusing RF energy at focus 107 within the target body. Phased array applicator 102 is energized by an RF energy source 108 having an RF output which is distributed to and drives each transmit antenna element $104_n$ through a corresponding transmit weighting function $(W_n)$ $110_n$, each having a corresponding voltage controlled RF power amplifier $P_n$ and a voltage controlled RF phase shifter $\phi_n$. Each weighting function may affect the power and phase of the RF energy fed to its corresponding antenna element $104_n$ in the array. An amplitude control voltage representing the amplitude component of the transmit weight is fed to the voltage controlled amplifier, and a phase control voltage representing the phase of the transmit weight is fed to the voltage controlled phase shifter.

Target body 106 has a plurality of E-field/temperature probes $112_m$, where m=1, . . . , $N_{aux}$, i.e., receiving antennas, positioned at various locations on the surface of the body for sampling the E-field at each particular location. Another invasive probe 115 is placed at the desired focus of the array, e.g., within the tumor.

Receiving probes $112_m$ and 115 each drive an input to an RF receiver 114. The transmit amplitude and phase weights of each weighting function $110_n$ are fed to the receiver 114 through lines $103_n$ and are used to find the transmit level of each transmit antenna element $104_n$. The outputs 117 of the receiver 114 represent the probe-received complex voltages, the focus probe-received complex voltage, and the transmit level of the phased array. The receiver outputs drive the inputs of a signal processor or computer 116, which applies a gradient search adaptive nulling/focusing algorithm to adjust the weighting functions $110_n$ and thereby null, or minimize, the RF signal received by each receiving probe $112_m$, i.e., minimize the $SNR_P$ at each probe. At RF frequencies between about 50 and 150 MHz, the adaptive nulls formed on the surface of the target body penetrate into the body to protect healthy tissue away from the tumor.

To generate the desired field distribution in a system in accordance with the invention, the receiving probes are positioned as close as possible to the focus (the tumor site) and to where high temperatures are to be avoided (such as near the spinal cord, scar tissue or other healthy tissue). For an annular array configuration, the receiving probes can be located non-invasively on the surface (skin) of the target. Initially, the array is focused to produce the required field intensity at the tumor. The invasive probe 115 is used to achieve the optimum focus at depth. To avoid undesired hot spots, it is necessary to minimize the power received at the desired null positions and to constrain the array transmit weights $110_n$ to deliver a required amount of transmitted or focal region power.

Signal processor 116 performs either a sample matrix inversion (SMI) algorithm or a gradient search algorithm on the signals output 117 from the receiver 114 and updates the adaptive array weights $110_n$ (with gain P and phase $\phi$) to rapidly form the nulls at the probes $112_m$ before a significant amount of target heating takes place. With the adaptive system of the invention, it is possible to avoid unintentional hot spots in the proximity $120_m$ of the probes $112_m$ and maintain a therapeutic thermal dose distribution at the focus 107 (tumor).

Signal processor 116 can also perform a maximizing algorithm to maximize energy at the focus 107. The focus probe 115 is invasively placed at the desired focus 107, and used to generate a maximum signal, or signal-to-noise ratio ($SNR_F$), at the tumor site. RF receiver 114 makes an amplitude and phase measurement on the output signal from invasive probe 115 for each transmit antenna element $104_n$ radiating one at a time. Signal processor 116 processes these measurements and feeds back weight command signals to the transmit weighting functions $110_n$ to calibrate or phase align the transmit channels to thereby maximize the $SNR_F$, or RF power, at the invasive focal point probe. If receiver 114 makes amplitude-only measurements from invasive focus probe 115, then a gradient search technique can be applied by the signal processor with all elements transmitting simultaneously to maximize the $SNR_F$ at the invasive focus probe 115.

The liposomes 122 are injected into the blood stream and are carried by blood flow into the heated area, where the liposomes release the pharmaceutical agent 124.

EXPERIMENTAL RESULTS

Figure 3:
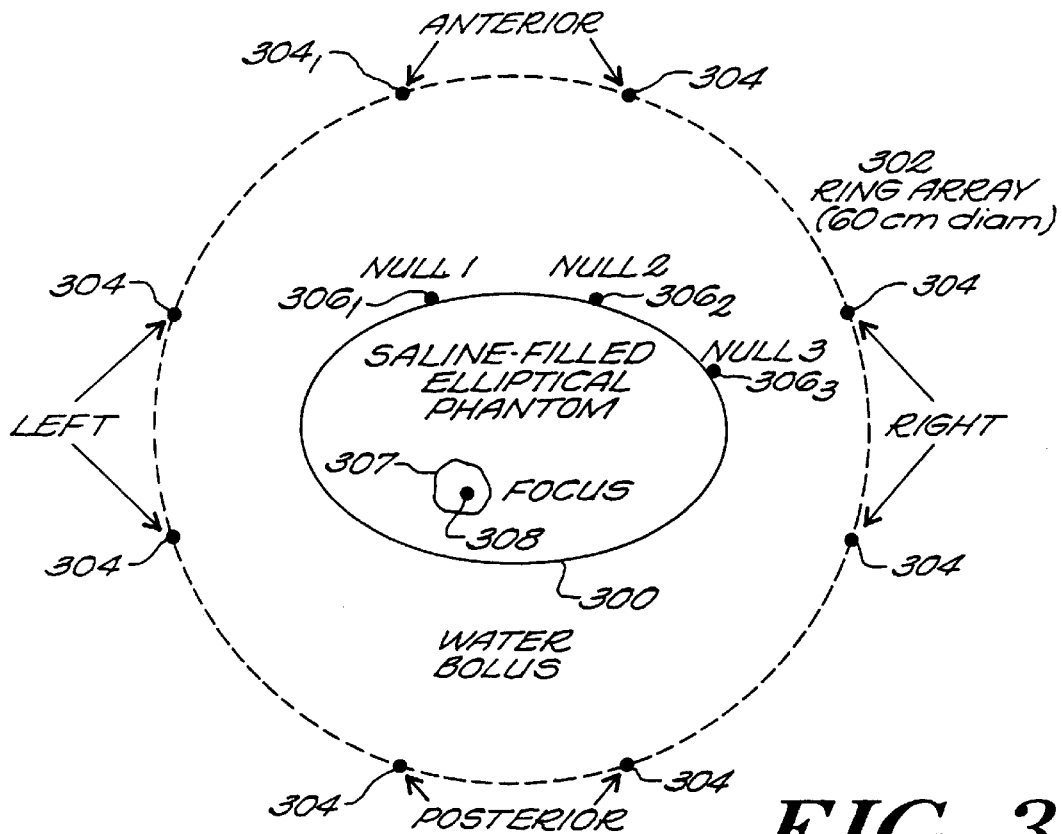
FIG. 3 is a schematic diagram of the cross-sectional geometry of an experiment conducted on adaptive nulling measurements performed on a four-channel RF thermodynamic adaptive phased array system at 100 MHz.

Adaptive nulling measurements were performed on a four-channel RF thermodynamic adaptive phased array system at 100 MHz. FIG. 3 is a schematic diagram of the cross-sectional geometry of the experiment conducted. An elliptical phantom human torso simulator 300 having width 36 cm, height 24 cm, and length 100 cm was used in the experiment. The phantom torso was surrounded by a commercial dipole phased array 302 having a diameter of 60 cm and a plurality of dipole antenna elements $304_1$–$304_4$ (BSD 2000 Hyperthermia System with Sigma 60 applicator, BSD Medical Corporation, Salt Lake City, Utah, USA) as described in P. F. Turner, A. Tumeh, and T. Schaefermeyer, "BSD-2000 Approach for Deep Local and Regional Hyperthermia: Physics and Technology", Strahlentherapie Onkologie, Vol. 165, No. 10, pp. 738–741, 1989. The elliptical phantom torso was filled with saline that models human muscle tissue. Dielectric losses of the saline were such that at 100 MHz the RF attenuation was about 1 dB per cm.

At 100 MHz, the RF wavelength in the saline solution is approximately 30 cm. The half-power beam diameter (or null diameter) of an adaptive ring array is approximately equal to one-half the wavelength or 15 cm. Thus, an intense null formed on the surface of the phantom should reduce the electric-field about 50-percent as much at a depth of 15 cm. Less intense nulls would have less effect on reducing the electric field intensity at depth. The outer shell of the elliptical phantom was made of 2 mm thick PVC (polyvinylchloride) hard plastic material which has electrical properties similar to human fat. Three electric field nulling sensors $306_1$–$306_3$ were positioned on the outer surface of the phantom as shown in FIG. 3. The objective of the experiment was to maintain a focused electric field on a deep seated simulated tumor position 307 8 cm beneath the surface of the phantom. To monitor the electric field at the tumor position, an invasive electric field sensor 308 was used.

The power and phase input to each of the four RF radiating antennas of the ring array were manually set to equal values at the start of the experiment. The sum of the input power to all four channels was held constant at 860 W during the experiment. The computer started the adaptive-array algorithm by automatically adjusting, via digital-to-analog converters, the power amplifiers and phase shifters in each of the four channels of the phased array. The computer software performed calculations of the rate of change of the measured RF power at the surface sensors (simulated healthy tissue regions) after each adjustment of RF power and phase to the array transmit channels. For this experiment, the method of steepest descent gradient search algorithm was used to determine the input power and phase commands that minimize the summation of the local power deposition measured by each surface electric-field feedback sensor. The gradient search computer algorithm iterated through sets of power and phase commands that adaptively nulled the RF power deposition on the surface of the phantom.

Figure 4:
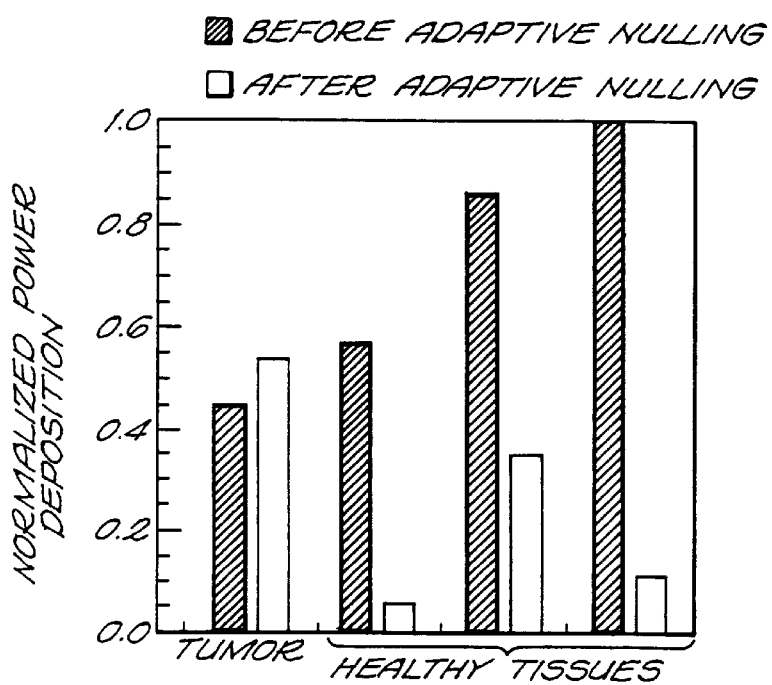
FIG. 4 is a graph of the measured RF power deposition at the four electric field sensors before and after adaptive nulling.

The measured RF power deposition at the four electric field sensors before and after adaptive nulling is shown in the graph of FIG. 4. Before nulling, the RF power deposition is significantly higher in the simulated healthy tissues compared to the RF power delivered to the simulated tumor position. After nulling, the electric field on the surface has been substantially reduced and the tumor RF power has increased by about 10 percent. These data demonstrate that the adaptive nulling thermodynamic phased array can heat a deep seated tumor while sparing healthy tissue. These data suggest that with an adaptive nulling thermodynamic phased array, thermosensitive liposomes can be targeted for delivery in certain regions but not in others.

After each iteration of the electric-field gradient search adaptive nulling algorithm, the total RF power must be adjusted to set the desired temperature within the tumor. In order to generate temperatures in the range that activate the thermosensitive liposomes, the RF power level delivered by the RF source is controlled adaptively based on feedback from an invasive temperature sensor (or the average temperature measured by several sensors) in the tissue to be heated.

Recent developments in non-invasive thermometry may eliminate the need for invasive temperature measurements. For example, magnetic resonance imaging, radiometry, applied potential tomography, and ultrasound are receiving considerable attention for non-invasive thermometry. Any of these non-invasive thermometry techniques can be used to supply temperature feedback for the adaptive phased array.

In an exemplary embodiment of the invention, radiation frequencies range between 50 and 150 MHz for deep torso heating. For head, neck, and breast heating, exemplary radiation frequencies range between 915 MHz and 2450 MHz, which are included in the Industrial, Scientific, and Medical (ISM) Equipment Bands of 902 to 928 MHz and 2400 to 2500 MHz (authorized by the International Telecommunications Union (ITU)) as described in DeGauque et al., *Electromagnetic Compatibility*, Oxford Univ. Press, 1993, p. 136. The frequency 434 MHz has also been used for superficial hyperthermia.

In an exemplary embodiment of the invention, a microwave radiating antenna is a monopole phased array consisting of monopole radiators contained within a water-filled metallic waveguide generally of elliptical or circular cross section. The length of each monopole radiator is approximately one-quarter wavelength at the desired radiating frequency.

In an exemplary embodiment of the invention, an invasive electric-field probe is a flexible sub-miniature metallic coaxial cable (RG-034) that has a 1 mm outer diameter with the outer jacket removed over a 1 cm tip area forming a monopole receive antenna. This electric field probe would be placed within a catheter. Although the metallic coaxial cable will scatter RF fields from the RF phased array, the adaptive nulling and focusing algorithm compensates for this scattering. It is known that metallic structures can be heated by RF fields, thus it may be necessary to water cool the catheter containing the coaxial cable. No cooling would be required within the tumor since heating due to the metallic coaxial cable assists in the tumor heating. Fiber-optics based electric-field probes would be good for this application, as they will scatter less energy and are not heated by RF fields.

For invasive temperature measurements within the body, an exemplary embodiment of the invention includes a temperature measurements probe which is a fiber-optics based device such as that commercially available from Luxtron Corporation, Santa Clara, Calif., USA, having a diameter typically 0.75 mm. Such a fiber-optics based temperature probe does not couple to RF fields so as not to interfere with the adaptive phased array electric field measurements. This temperature probe can be placed within the same catheter as the above invasive electric field probe.

The concept of a minimally invasive adaptive-nulling RF phased array thermodynamic system is shown in the schematic block diagram of FIG. 2. Theoretically, to generate the desired field distribution in a clinical adaptive thermodynamic system, receiving sensors are positioned as close as possible to the focus (tumor site) and where high temperatures are to be avoided (such as near the spinal cord and scar tissue). A noninvasive adaptive nulling system is achieved by placing auxiliary sensors $1, 2, \ldots, N_{aux}$ on the target skin as shown. The null zones centered at each auxiliary probe naturally extend into the elliptical target region to eliminate undesired hot spots.

The width of each null zone is directly related to the strength of each null. The strength of each null (sometimes referred to as the amount of cancellation) is directly related to the SNR at the sensor position. A low SNR produces a small amount of nulling, a high SNR a large amount of nulling. The resolution or minimum spacing between the focus and null positions is normally equal to the half-power beamwidth of the antenna. The resolution is enhanced somewhat by using weak nulls whenever the separation between the null and focus is closer than the half-power beamwidth.

The half-power angular beamwidth of a focused antenna aperture with diameter D in wavelengths is approximated by $$\theta_{HPBW} = \lambda/D \quad (4)$$

where $\lambda$ is the wavelength. The antenna half-power focal beamwidth (spot size) in units of length is expressed as $$s = \theta_{HPBW} \times R \quad (5)$$

where R is the focal distance of the antenna. Using Equation (4) and substituting R=D/2 for a ring array focused at the origin in Equation (5) yields:

$$s = \lambda/2 \quad (6)$$

Thus, the approximate focal spot size or resolution of a ring array is one-half the wavelength in the target body and can be confirmed via computer simulation.

Initially, the thermodynamic phased array of the invention is phase focused to produce the required field intensity at the tumor. An invasive probe is required to achieve the optimum focus at depth. To avoid hot spots, it is necessary to minimize the power received at the desired null positions and to constrain the array weights to deliver a required amount of transmitted or focal-region power.

The adaptive array weights (with gain g and phase $\Phi$) are controlled by either the SMI algorithm or a gradient-search algorithm to rapidly form the nulls before a significant amount of target heating takes place. With this adaptive technique, it should be possible to avoid hot spots and maintain a therapeutic thermal dose distribution at the tumor. Following the process of adaptive nulling, the phase focusing algorithm would again be applied to improve the focus at the tumor site.

ADAPTIVE TRANSMIT-ARRAY FORMULATION

Consider a thermodynamic phased array with N identical antenna elements. The input signal to each of the N array elements is obtained from the weighted signal distributed by a power divider network. The number of adaptive channels is denoted N. Let $w=(w_1, w_2, \ldots, w_N)^T$ denote the adaptive channel weight vector as shown in FIG. 2. The superscript T in the equation means transpose.

For an adaptive annular array focused at the origin in homogeneous tissue, the normalized quiescent weight vector is simply $w_q=(1, 1, 1 \ldots, 1)^T$. In other words, the amplitude and phase illumination are uniform. Commonly, the weight vector is constrained to deliver a required amount of power to the thermodynamic phased array or to the tumor. For simplicity in the experimental adaptive-thermodynamic-array control software, the weights are constrained such that $$\sum_{n=1}^{N} |w_n| = K \tag{7}$$

where $|w_n|$ is the transmit-weight amplitude for the nth adaptive channel and K is a constant. To generate adaptive nulls, the transmit weights (phase and amplitude) are controlled by either the SMI algorithm or a gradient-search algorithm. The SMI algorithm has the flexibility to operate in either open- or closed-loop feedback modes. The gradient-search algorithm operates only in a feedback mode.

GRADIENT-SEARCH ADAPTIVE ARRAY ALGORITHM

Gradient-search algorithms are commonly used in adaptive-array applications where the channel correlation cannot be calculated or measured. With a gradient search, only the output power of the receiver channels needs to be measured and is used as a feedback signal to the algorithm. A wide variety of gradient searches exist.

Under conditions where only the probe-received power is measured, it is appropriate to consider a gradient-search algorithm to minimize the E-field power at selected positions. The gradient search is used to control the transmit weights iteratively so that the RF signal received by the probe array is minimized. The transmit-array weights (amplitude and phase) are adaptively changed in small increments and the probe-array output power is monitored to determine weight settings that reduce the output power most rapidly to a null. The mathematical formulation for the gradient search is developed in a straightforward manner and are hereinafter described in the context of thermodynamic therapy. Although the mathematical formulation is given as a minimization (adaptive nulling) problem, the equations are readily converted to the maximization (adaptive focusing) problem.

The summation of power received at the electric-field probes is denoted by $p^{rec}$. The adaptive array cancellation ratio, denoted C, is defined here as the ratio of the summation of probe-received power after adaption $p_a$ to the summation of probe-received power before adaption $p_b$; that is, $$C = \frac{p_a}{p_b}. \tag{8}$$

Consider now J sets (or iterations) of N transmit weights that are applied to an adaptive thermodynamic phased-array antenna. In terms of adaptive nulling, the optimum transmit-weight settings (from the collection of J sets of N transmit weights) occur when the total interference power (or power in the healthy tissue) received by the auxiliary probe array, denoted $p^{rec}$, is minimized. For notational convenience let a figure of merit F denote $p^{rec}$ and employ a method of steepest-descent gradient search to find the optimum transmit weights to minimize F; that is, $$F_{opt}=\min(F_j) \; j=1,2,\ldots,j. \tag{9}$$

Figure 5:
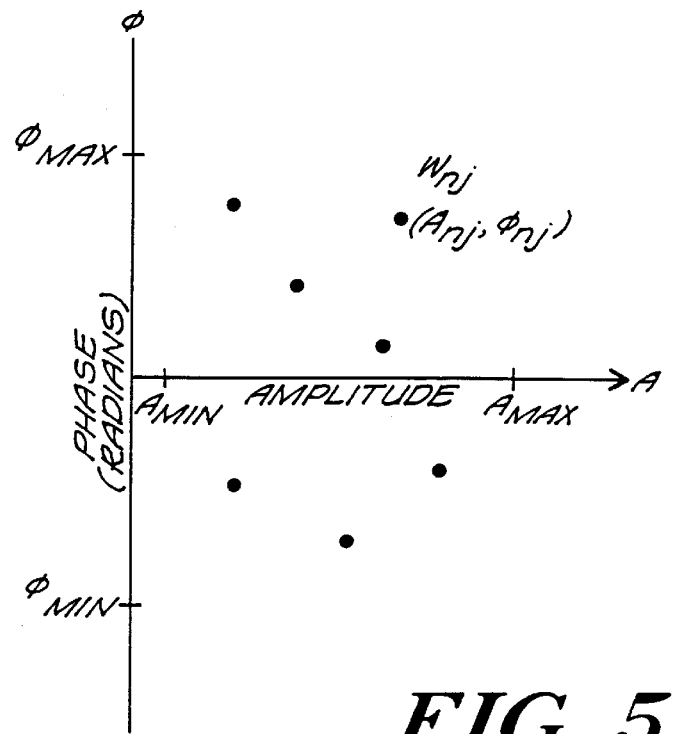
FIG. 5 is an amplitude and phase scatter diagram for N complex transmit weights in the thermodynamic phased array of the invention.

Assume that there are N complex transmit weights in the thermodynamic phased array as suggested by the amplitude and phase scatter diagram depicted in FIG. 5. The nth transmit weight in the jth configuration (or iteration) of transmit weights is denoted $$W_{nj}=A_{nj}e^{j\Phi_{nj}} \tag{10}$$

where $A_{nj}$ is the transmit-weight amplitude distributed over the range $A_{min}$ to $A_{max}$ and $\Phi_{nj}$ is the transmit-weight phase distributed over the range $\Phi_{min}$ to $\Phi_{max}$. The goal is to find the values of amplitude and phase for each of the N transmit weights such that the figure of merit ($p^{rec}$) is minimized. When the figure of merit is minimized, adaptive radiation pattern nulls will be formed at the auxiliary sensor positions.

Assuming an initial setting of the N transmit weights, the weights are adjusted by dithering them until the optimum figure of merit is achieved. The goal is to find the collective search directions for the N transmit weights such that F decreases most rapidly. That is, transmit weights are selected so that the directional derivative is minimized at $(A_j, \Phi_j)$, where $A_j$ and $\Phi_j$ are the amplitude and phase column vectors, respectively.

The directional derivative of $F_j$ is expressed in terms of the amplitude and phase changes of the transmit weights as $$D(F_j) = \sum_{n=1}^{N} \left( \frac{\partial F_j}{\partial A_{nj}} r_{Anj} + \frac{\partial F_j}{\partial \Phi_{nj}} r_{\Phi nj} \right), \tag{11}$$

where $\partial$ means partial derivative and $r_{Anj}, R_{\Phi nj}$ are the $(A, \Phi)$ directions for which $F_j$ is decreasing most rapidly. The directions $r_{Anj}, r_{\Phi nj}$ are constrained by $$\sum_{n=1}^{N} (r_{Anj}^2 + r_{\Phi nj}^2) = 1 \tag{12}$$

The goal is to minimize $D(F_j)$ subject to the above constraint equation.

Using Lagrange multipliers, construct the Lagrangian function $$L_j = \sum_{n=1}^{N} \left( \frac{\partial F_j}{\partial A_{nj}} r_{Anj} + \frac{\partial F_j}{\partial \Phi_{nj}} r_{\Phi nj} \right) + G \left[ 1 - \sum_{n=1}^{N} (r_{Anj}^2 + r_{\Phi nj}^2) \right], \tag{13}$$

where G is a constant to be determined. The requirement that $L_j$ be an extremum implies $$\frac{\partial L_j}{\partial r_{Anj}} = \frac{\partial F_j}{\partial A_{nj}} - 2Gr_{Anj} = 0, \quad n = 1, 2, \ldots, N \tag{14}$$

$$\frac{\partial L_j}{\partial r_{\Phi nj}} = \frac{\partial F_j}{\partial \Phi_{nj}} - 2Gr_{\Phi nj} = 0, \quad n = 1, 2, \ldots, N, \tag{15}$$

or $$r_{Anj} = \frac{1}{2G} \frac{\partial F_j}{\partial A_{nj}} \tag{16}$$

$$r_{\Phi nj} = \frac{1}{2G} \frac{\partial F_j}{\partial \Phi_{nj}}. \tag{17}$$

Squaring Equations (16) and (17), and invoking Equation (12) yields $$\sum_{n=1}^{N} (r_{Anj}^2 + r_{\Phi nj}^2) = 1 = \frac{1}{4G^2} \sum_{n=1}^{N} \left[ \left( \frac{\partial F_j}{\partial A_{nj}} \right)^2 + \left( \frac{\partial F_j}{\partial \Phi_{nj}} \right)^2 \right]; \tag{18}$$

thus, $$G = \pm \frac{1}{2} \sqrt{\sum_{n=1}^{N} \left[ \left( \frac{\partial F_j}{\partial A_{nj}} \right)^2 + \left( \frac{\partial F_j}{\partial \Phi_{nj}} \right)^2 \right]} \quad (19)$$

Substituting Equation (19) into Equations (16) and (17) gives $$r_{Anj} = -\frac{\frac{\partial F_j}{\partial A_{nj}}}{\sqrt{\sum_{n=1}^{N} \left[ \left( \frac{\partial F_j}{\partial A_{nj}} \right)^2 + \left( \frac{\partial F_j}{\partial \Phi_{nj}} \right)^2 \right]}} \quad (20)$$

$$r_{\Phi nj} = -\frac{\frac{\partial F_j}{\partial \Phi_{nj}}}{\sqrt{\sum_{n=1}^{N} \left[ \left( \frac{\partial F_j}{\partial A_{nj}} \right)^2 + \left( \frac{\partial F_j}{\partial \Phi_{nj}} \right)^2 \right]}}. \quad (21)$$

In Equations (20) and (21) the minus sign was chosen corresponding to the direction of maximum function decrease. It will be appreciated that by changing the minus sign to a plus sign in Equations (20) and (21), the search directions then correspond to the direction of maximum function increase, i.e., the plus sign is used to maximize the power delivered to the focus or tumor site. The partial derivatives $$\frac{\partial F_j}{\partial A_{nj}}, \frac{\partial F_j}{\partial \Phi_{nj}}; \quad n = 1, 2, \ldots, N \quad (22)$$

represent the gradient directions for maximum function decrease.

Figure 6:
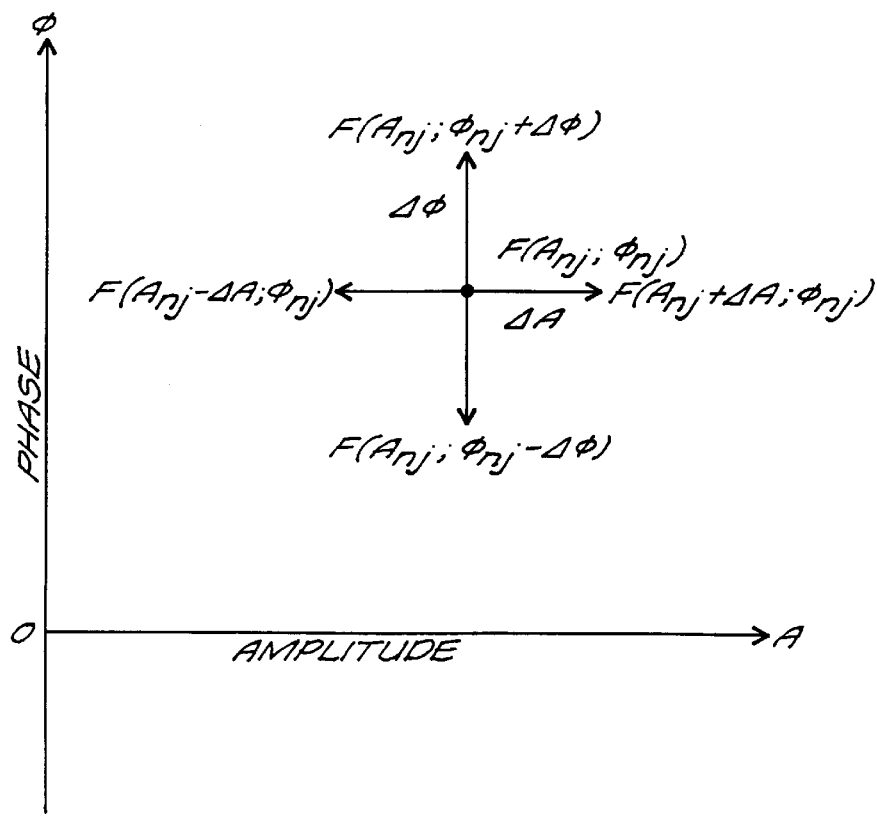
FIG. 6 is a graph of the figure of merit with transmit-weight dithering for optimum search directions.

Because the figure of merit F is measured and cannot be expressed in analytical form, the partial derivatives are numerically evaluated using finite differences. Thus, $$\frac{\partial F_j}{\partial A_{nj}} = \frac{\Delta F_{Anj}}{2\Delta A_{nj}} \quad (23)$$

$$\frac{\partial F_j}{\partial \Phi_{nj}} = \frac{\Delta F_{\Phi nj}}{2\Delta \Phi_{nj}}, \quad (24)$$

where, as shown in FIG. 6, $$\Delta F_{Anj} = F_j(A_{nj} + \Delta A_{Anj}; \Phi_{nj}) - F_j(A_{nj} - \Delta A_{nj}; \Phi_{nj}) \quad (25)$$

$$\Delta F_{\Phi nj} = F_j(A_{nj}; \Phi_{nj} + \Delta \Phi_{nj}) - F_j(A_{nj}; \Phi_{nj} - \Delta \Phi_{nj}) \quad (26)$$

and $\Delta A_{nj}$ and $\Delta \Phi_{nj}$ are the maximum step sizes. Assume for now that the increments and $\Delta A_{nj}$ and $\Delta A \Phi_{nj}$ depend on the iteration number j and transmit element index n. Substituting Equations (23) and (24) into Equations (20) and (21) gives the desired result for the search directions:

$$r_{Anj} = -\frac{\frac{\Delta F_{Anj}}{\Delta A_{nj}}}{\sqrt{\sum_{n=1}^{N} \left[ \left( \frac{\Delta F_{Anj}}{\Delta A_{nj}} \right)^2 + \left( \frac{\Delta F_{\Phi nj}}{\Delta \Phi_{nj}} \right)^2 \right]}} \quad (27)$$

$$r_{\Phi nj} = -\frac{\frac{\Delta F_{\Phi nj}}{\Delta \Phi_{nj}}}{\sqrt{\sum_{n=1}^{N} \left[ \left( \frac{\Delta F_{Anj}}{\Delta A_{nj}} \right)^2 + \left( \frac{\Delta F_{\Phi nj}}{\Delta \Phi_{nj}} \right)^2 \right]}}. \quad (28)$$

The new amplitude and phase settings of the (j+1)th transmit-weight configuration are computed according to $$A_{n,j+1} = A_{nj} + \Delta A_{nj} r_{Anj} \quad (29)$$

$$\Phi_{n,j+1} = \Phi_{nj} + \Delta \Phi_{nj} r_{\Phi nj}. \quad (30)$$

For the current software implementation of the gradient search in these experiments, assume (for convenience) that the step sizes are independent of both the iteration number and the adaptive channel number; that is, $$\Delta A_{nj} = \Delta A \quad (31)$$

$$\Delta \Phi_{nj} = \Delta \Phi. \quad (32)$$

In some situations it may be desirable to change the step size at each iteration, but that possibility has not been explored in these measurements.

FAST-ACCELERATION ALGORITHM

To speed the convergence of the gradient search, Equations (29) and (30) are replaced as follows:

The fast-acceleration amplitude and phase settings of the current jth transmit-weight configuration are computed by introducing sub-iterations denoted as the index k, k=1,2,3, . . . , .

$$A_{n,j,k} = A_{nj} + \Delta A_{nj} r_{Anj} 2^{k-1} \quad (33)$$

$$\Phi_{n,j,k} = \Phi_{nj} + \Delta \Phi_{nj} r_{\Phi nj} 2^{k-1}. \quad (34)$$

In other words, at each iteration j, the algorithm starts a sub-iteration k that changes the amplitude and phase increments in increasing powers of 2. It will be appreciated that other values besides 2 could be used, such as 3, 4, etc. To be more explicit, the index IFAST is used to replace k. When, the sub-iteration is started, k=1 and the adaptive array weights $A_{n,j,1}$ and $\Phi_{n,j,1}$ are calculated and set via the digital-to-analog converters in the hardware and the electric-field probe powers $p_{j,k,i}^{rec}$, i=1,2,3, . . . at iteration j and sub-iteration k are measured and stored in the computer. The algorithm can be made to stop when either the individual electric-field probe powers reach desired null-strength values or when the summation of the probe powers reaches a desired null-strength value. During the next sub-iteration, k=2, and the adaptive array weights $A_{n,j,2}$ and $\Phi_{n,j,2}$ are computed according to Equations (33) and (34). These new weights are set by the hardware and the probe powers $p_{j,k,i}^{rec}$, i=1,2,3, . . . at iteration j and sub-iteration k=2 are measured and stored in the computer.

For adaptive nulling, if $$\sum_{i=1}^{N_{aux}} p_{j,k=2,i}^{rec} < \sum_{i=1}^{N_{aux}} p_{j,k=1,i}^{rec} \quad (35)$$

then the summation of probe power has decreased and the sub-iterations continue by incrementing k to 3 and proceeding in the same manner. That is, compute and set $A_{n,j,3}$ and $\Phi_{n,j,3}$, measure the received probe powers and compare the magnitude of $\Sigma p_{j,k=3,i}^{rec}$ with $\Sigma p_{j,k=2,i}^{rec}$ as in the previous case. However, if $$\Sigma p_{j,k=2,i}^{rec} > \Sigma p_{j,k=1,i}^{rec} \quad (36)$$

then the summation of probe power has increased and the sub-iterations stop and the next iteration for j continues.

For the fast-acceleration gradient search assume (for convenience) that the step sizes are independent of both the iteration number and the adaptive channel number; that is, $$\Delta A_{nj} = \Delta A \quad (37)$$

$$\Delta \Phi_{nj} = \Delta \Phi \quad (38)$$

SYSTEM CONSIDERATIONS

Figure 7:
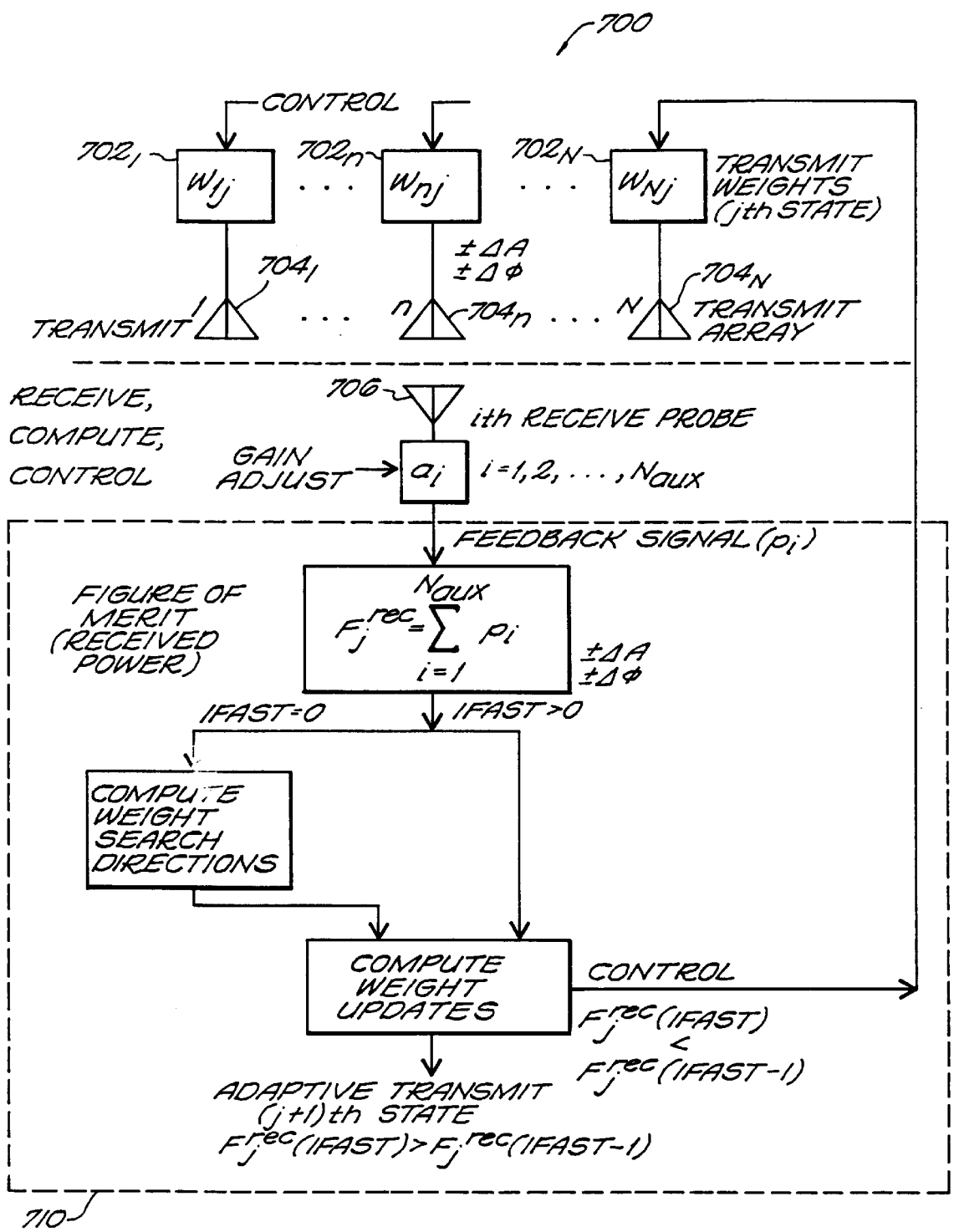
FIG. 7 is a block diagram for an adaptive-nulling thermodynamic system controlled by the fast-acceleration gradient-search algorithm in accordance with an exemplary embodiment of the invention.

FIG. 7 is a block diagram for an adaptive-nulling thermodynamic system 700 controlled by the fast-acceleration gradient-search algorithm in accordance with an exemplary embodiment of the invention. The transmit weights $w_{1j}, \ldots, w_{nj}, \ldots, w_{Nj}$ (702$_1$–702$_N$) at the jth iteration are shown at the top of the figure. The transmit phased-array antenna (704$_1$–704$_N$) induces a voltage across the terminals of the ith receive field probe antenna 706 with gain adjust 708. For any given configuration of the transmit weights, each weight is dithered by a small amount in amplitude and phase and the received powers at the electric-field probes are stored in a computer 710 for calculation of the figure of merit, search directions, and updated (j+1)th transmit-weight configuration.

The weight dithering of one transmit weight must be done with the remaining transmit weights in their jth state. The figure of merit $F_j$ in the adaptive thermodynamic system is the power received by the auxiliary probe array, as indicated in the block diagram. The figure of merit is a rectangular matrix with dimensions (N×4). A dimensionality of four is due to the plus and minus dithering of both amplitude and phase. Search directions for the adaptive transmit weights are based on minimizing the auxiliary-probe-array received power and are computed based on Equations (27) and (28). The transmit weights for the next configuration (j+1) are computed from Equations (29) and (30). The adaptive weight vector $w_a$ is achieved when the (j+1)th weight configuration has converged. The fast acceleration algorithm converges in just a few iterations.

While the invention has been particularly shown and described with references to illustrated exemplary embodiments thereof, it will be understood by those skilled in the art that various changes in form and details may be made therein without departing from the spirit and scope of the invention as defined by the appended claims. For instance, the apparatus described herein is applicable from low RF frequencies to millimeter wave frequencies as well as ultrasound. The preferred radiating element is a monopole, however, it is recognized that other radiating elements such as a dipole, helix, microstrip patch, waveguide or any other radiator can be used in the adaptive phased array. While this disclosure has referred to one particular type of liposome, it is recognized that other liposomes may be developed and can be targeted for delivery by the thermodynamic adaptive phased array system described herein. Still further, the invention is applicable to non-medical hyperthermia systems, such as those used for industrial materials heating.

What is claimed is:

1. A thermodynamic therapy system, comprising:
   a thermally activated drug delivery system which is provided within the bloodstream of a patient under therapy, said thermally activated drug delivery system comprising thermosensitive liposomes; and
   an adaptive phased array radiation transmission system operable for transmitting and focusing radiation to heat a treatment area within said patient, said adaptive phased array radiation transmission system including a fast acceleration gradient search algorithm to transmit and focus radiation, wherein
   said drug delivery system releases a selected drug at said treatment area in response to said treatment area being heated by said focused radiation.

2. The system of claim 1, wherein said thermosensitive liposomes encapsulate a desired pharmaceutical agent.

3. The system of claim 2, wherein said pharmaceutical agent comprises a chemotherapy agent.

4. The system of claim 2, wherein said pharmaceutical agent comprises a gene therapy agent.

5. The system of claim 2, wherein said thermosensitive liposomes undergo a phase transition at a predetermined temperature in order to release said pharmaceutical agents.

6. The system of claim 1, wherein said adaptive phased array radiation transmission system comprises:
   means for transmitting radiation;
   means for controlling the phase and amplitude of said radiation in response to feedback signals;
   means for detecting said radiation; and
   control means for receiving the detected radiation and generating said feedback signals, said control means further operable for adjusting said feedback signals in accordance with the detected radiation.

7. The system of claim 6, wherein said detecting means comprises a plurality of radiation probes disposed non-invasively along the skin surface of said patient.

8. The system of claim 7, wherein said control means adjusts said feedback signals so that the detected radiation is minimized at said plurality of probes.

9. The system of claim 8, wherein said control means performs said fast acceleration gradient search algorithm to generate said feedback signals.

10. The system of claim 9, wherein said control means comprises:
    means for receiving said radiation from at least an nth field radiator at an ith probe for a jth configuration of transmit weights $w_{nj}$;
    means for calculating a figure of merit $F_j^{rec}$ from the received radiation given by $$F_j^{rec} = \sum_{i=1}^{N_{aux}} p_i$$

where $N_{aux}$ is the number of probes;
    means for dithering the transmit weights $w_{nj}$ by a small amount in amplitude, $\Delta A_{nj}$, and phase, $\Delta \Phi_{nj}$;
    means for determining the figure of merit differences $\Delta F_{Anj}$ and $\Delta F_{\Phi nj}$ caused by dithering the amplitude and phase, respectively;
    means for determining gradient search directions $r_{Anj}$ and $r_{\Phi nj}$ given by $$r_{Anj} = -\frac{\frac{\Delta F_{Anj}}{\Delta A_{nj}}}{\sqrt{\sum_{n=1}^{N}\left[\left(\frac{\Delta F_{Anj}}{\Delta A_{nj}}\right)^2 + \left(\frac{\Delta F_{\Phi nj}}{\Delta \Phi_{nj}}\right)^2\right]}}$$

and $$r_{\Phi nj} = -\frac{\frac{\Delta F_{\Phi nj}}{\Delta \Phi_{nj}}}{\sqrt{\sum_{n=1}^{N}\left[\left(\frac{\Delta F_{Anj}}{\Delta A_{nj}}\right)^2 + \left(\frac{\Delta F_{\Phi nj}}{\Delta \Phi_{nj}}\right)^2\right]}}$$

respectively; and
    means for generating a new transmit weight $w_{n,(j+1),k}$ for the (j+1)th configuration and for sub-iterations k, where k=1,2,3, . . . , where the amplitude component of the new weight for the current jth configuration is given by $$A_{n,j,k} = A_{nj} + \Delta A_{nj} r_{Anj} 2^{k-1}$$

and the phase component of the new weight is given by $$\Phi_{n,j,k} = \Phi_{nj} + \Delta \Phi_{nj} r_{\Phi nj} 2^{k-1}.$$

11. The system of claim 6, wherein said detecting means comprises an radiation probe disposed at the desired focus of said transmission system.

12. The system of claim 11, wherein said control means adjusts said feedback signals so that the detected radiation is maximized at said probe.

13. The system of claim 1, wherein said radiation comprises electromagnetic radiation.

14. The system of claim 1, wherein said radiation comprises ultrasonic radiation.

15. A method of thermodynamically delivering a drug to a treatment area within a patient, comprising:

providing a thermally activated drug delivery system in the bloodstream of said patient, said thermally activated drug delivery system comprising thermosensitive liposomes; and transmitting and focusing radiation from an adaptive phased array transmission system to heat said treatment area within said patient, said adaptive phased array radiation transmission system including a fast acceleration gradient search algorithm to transmit and focus radiation, said drug delivery system releasing said drug at said treatment area in response to said treatment area being heated by said adaptively transmitted and focused radiation.

16. The method of claim 15, wherein said thermosensitive liposomes encapsulate a desired pharmaceutical agent.

17. The method of claim 16, wherein said pharmaceutical agent comprises a chemotherapy agent.

18. The method of claim 16, wherein said pharmaceutical agent comprises a gene therapy agent.

19. The method of claim 16, wherein said thermosensitive liposomes undergo a phase transition at a predetermined temperature in order to release said pharmaceutical agents.

20. The method of claim 15, wherein said step of transmitting and focusing further comprises:

transmitting radiation;

controlling the phase and amplitude of said radiation in response to feedback signals;

detecting said radiation by detecting means;

receiving the detected radiation;

generating said feedback signals; and adjusting said feedback signals in accordance with the detected radiation.

21. The method of claim 20, wherein said detecting means comprises a plurality of radiation probes disposed non-invasively along the skin surface of said patient.

22. The method of claim 20, wherein said detecting means comprises an radiation probe disposed at the desired focus of said transmission system.

23. The method of claim 22 further comprising adjusting said feedback signals so that the detected radiation is maximized at said probe.

24. The method of claim 21 further comprising adjusting said feedback signals so that the detected radiation is minimized at said plurality of probes.

25. The method of claim 24 further comprising performing said fast acceleration gradient search algorithm to generate said feedback signals.

26. The method of claim 25 further comprising:

receiving said radiation from at least an nth field radiator at an ith probe for a jth configuration of transmit weights $w_{nj}$;

calculating a figure of merit $F_j^{rec}$ from the received radiation given by $$F_j^{rec} = \sum_{i=1}^{N_{aux}} p_i$$

where $N_{aux}$ is the number of probes;

dithering the transmit weights $w_{nj}$ by a small amount in amplitude, $\Delta A_{nj}$, and phase, $\Delta \Phi_{nj}$;

determining the figure of merit differences $\Delta F_{Anj}$ and $\Delta F_{\Phi nj}$ caused by dithering the amplitude and phase, respectively;

determining gradient search directions $r_{Anj}$ and $r_{\Phi nj}$ given by $$r_{Anj} = -\frac{\frac{\Delta F_{Anj}}{\Delta A_{nj}}}{\sqrt{\sum_{n=1}^{N}\left[\left(\frac{\Delta F_{Anj}}{\Delta A_{nj}}\right)^2 + \left(\frac{\Delta F_{\Phi nj}}{\Delta \Phi_{nj}}\right)^2\right]}}$$

and $$r_{\Phi nj} = -\frac{\frac{\Delta F_{\Phi nj}}{\Delta \Phi_{nj}}}{\sqrt{\sum_{n=1}^{N}\left[\left(\frac{\Delta F_{Anj}}{\Delta A_{nj}}\right)^2 + \left(\frac{\Delta F_{\Phi nj}}{\Delta \Phi_{nj}}\right)^2\right]}}$$

respectively; and generating a new transmit weight $w_{n,(j+1),k}$ for the (j+1)th configuration and for sub-iterations k, where K=1,2,3, ..., where the amplitude component of the new weight for the current jth configuration is given by $$A_{n,j,k} = A_{nj} + \Delta A_{nj} r_{Anj} 2^{k-1}$$

and the phase component of the new weight is given by $$\Phi_{n,j,k} = \Phi_{nj} + \Delta \Phi_{nj} r_{\Phi nj} 2^{k-1}.$$

27. The method of claim 15, wherein said radiation comprises electromagnetic radiation.

28. The method of claim 15, wherein said radiation comprises ultrasonic radiation.

* * * * *